United States Patent [19]
Dewhurst

[11] Patent Number: 5,123,407
[45] Date of Patent: Jun. 23, 1992

[54] HIP ALIGNMENT GARMENT

[76] Inventor: Dennis K. Dewhurst, 7331 Pentz Rd., Paradise, Calif. 95969

[21] Appl. No.: 682,304

[22] Filed: Apr. 9, 1991

[51] Int. Cl.$^5$ .............................................. A61F 5/00
[52] U.S. Cl. ........................................ 602/2; 128/379; 128/882; 128/402; 2/23; 602/13; 602/62
[58] Field of Search ............... 128/68, 68.1, 69, 80 R, 128/80 A, 80 B, 845, 882, 891, 394–403, 379, 380; 62/259.3; 2/2, 23, 78 B, 78 C, 233

[56] References Cited

U.S. PATENT DOCUMENTS

| | | | |
|---|---|---|---|
| 2,568,083 | 9/1951 | Mitchell | 2/23 |
| 2,867,215 | 1/1959 | Horton et al. | 128/399 |
| 3,508,550 | 4/1970 | Vollrath | 128/891 |
| 4,607,629 | 8/1986 | Lerman | 128/80 A |

FOREIGN PATENT DOCUMENTS 126023 12/1901 Netherlands ............................ 2/233

Primary Examiner—Benjamin Layno
Assistant Examiner—Mark S. Graham
Attorney, Agent, or Firm—Leon Gilden

[57] ABSTRACT

A garment including a torso portion includes a right and left leg, with the right and left leg including arcuate confronting surfaces. The right confronting surfaces mount wedge-shaped pads therewithin to maintain proper spacing of an individual's upper leg portions for corrective alignment during sleep of an individual. A modification of the invention includes pockets arranged for receiving the wedge-shaped members which may be in the form of pneumatic chamber. Optionally, rheostat heating pad structure is directed within the garment directed coextensively adjacent and in contiguous communication with the right and left pockets.

3 Claims, 4 Drawing Sheets

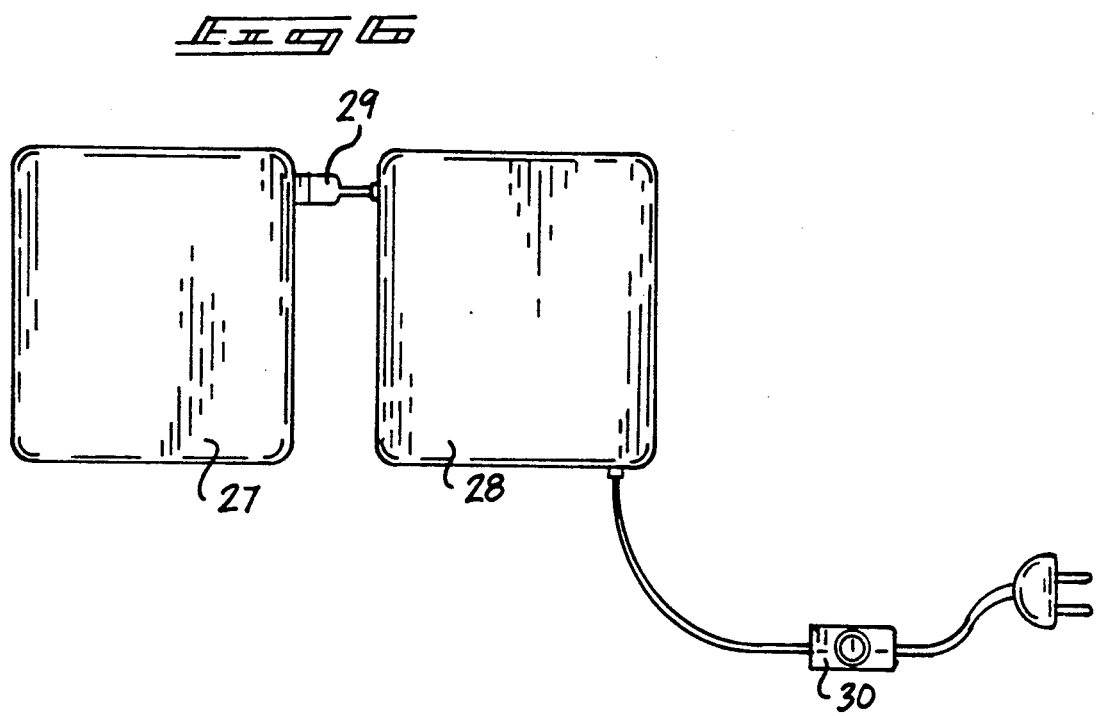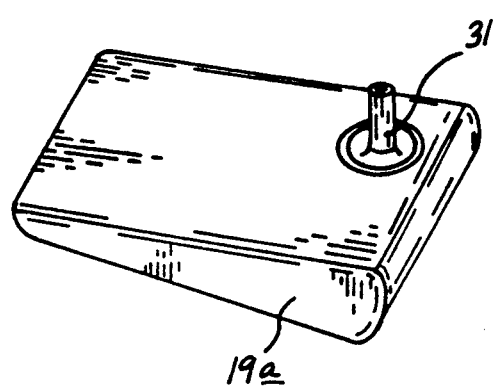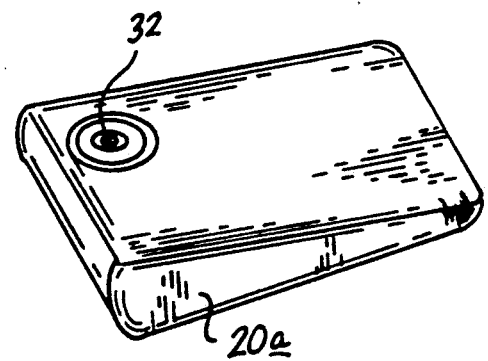

HIP ALIGNMENT GARMENT

BACKGROUND OF THE INVENTION

1. Field of the Invention

The field of invention relates to padded garment structure, and more particularly pertains to a new and improved hip alignment garment wherein the same is arranged to properly space and individual's legs for maintaining spacing during slumber for corrective hip alignment during such conditions.

2. Description of the Prior Art

Various padded garments are utilized in the prior art to typically provide padding encountered during impact. The instant invention is set apart from the prior art by utilizing such padding to properly space interior surfaces of an individual's confronting leg surfaces for maintaining proper alignment of the individual's legs for corrective hip and back alignment, particularly during slumber. Examples of the prior art include U.S. Pat. No. 2,568,083 to Mitchell setting forth knee patches removably mounted within a pants structure.

U.S. Pat. No. 4,479,269 to Balliet sets forth athletic padding mounted to various forward surfaces of leg portions of an athletic type garment, such as utilized in football.

U.S. Pat. No. 4,561,124 to Thompson sets forth knee padding to be utilized in work pants.

U.S. Pat. No. 4,831,666 to Denman sets forth a garment utilizing a further example of knee padding positionable within pockets within the knee structure.

As such, it may be appreciated that there continues to be a need for a new and improved hip alignment garment as set forth by the instant invention which addresses both the problems of ease of use as well as effectiveness in construction in maintaining proper alignment of an individual's hips and legs during slumber and in this respect, the present invention substantially fulfills this need.

SUMMARY OF THE INVENTION

In view of the foregoing disadvantages inherent in the known types of padded garment structure now present in the prior art, the present invention provides a hip alignment garment wherein the same is utilized with confronting wedge-shaped pad members mounted to interior surfaces of right and left legs of a pants leg garment utilized by an individual for corrective hip alignment during slumber. As such, the general purpose of the present invention, which will be described subsequently in greater detail, is to provide a new and improved hip alignment garment which has all the advantages of the prior art padded garment structures and none of the disadvantages.

To attain this, the present invention provides a garment including a torso portion, with a right and left leg, with the right and left leg including arcuate confronting surfaces. The right confronting surfaces mount wedge-shaped pads therewithin to maintain proper spacing of an individual's upper leg portions for corrective alignment during sleep of an individual. A modification of the invention includes pockets arranged for receiving the wedge-shaped members which may be in the form of pneumatic chamber. Optionally, rheostat heating pad structure is directed within the garment directed coextensively adjacent and in contiguous communication with the right and left pockets.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved hip alignment garments which has all the advantages of the prior art padded garment structures and none of the disadvantages.

It is another object of the present invention to provide a new and improved hip alignment garment which may be easily and efficiently manufactured and marketed.

It is a further object of the present invention to provide a new and improved hip alignment garment which is of a durable and reliable construction.

An even further object of the present invention is to provide a new and improved hip alignment garment which is susceptible of a low cost of manufacture with regard to both materials and labor, and which accordingly is then susceptible of low prices of sale to the consuming public, thereby making such hip alignment garments economically available to the buying public.

Still yet another object of the present invention is to provide a new and improved hip alignment garment which provides in the apparatuses and methods of the prior art some of the advantages thereof, while similtaneously overcoming some of the disadvantages normally associated therewith.

Still another object of the present invention is to provide a new and improved hip alignment garment wherein the same is arranged for readily mounting to an individual during slumber for maintaining proper alignment of an individual's hip and leg portions.

These together with other objects of the invention, along with the various features of novelty which characterize the invention, are pointed out with particularity in the claims annexed to and froming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is an orthographic view of the heating pad structure utilized by the instant invention.

FIGS. 7 and 8 are isometric illustrations of respective right and left wedge-shaped pneumatic pads utilized by the instant invention.

DESCRIPTION OF THE PREFERRED EMBODIMENT

Figure 1:
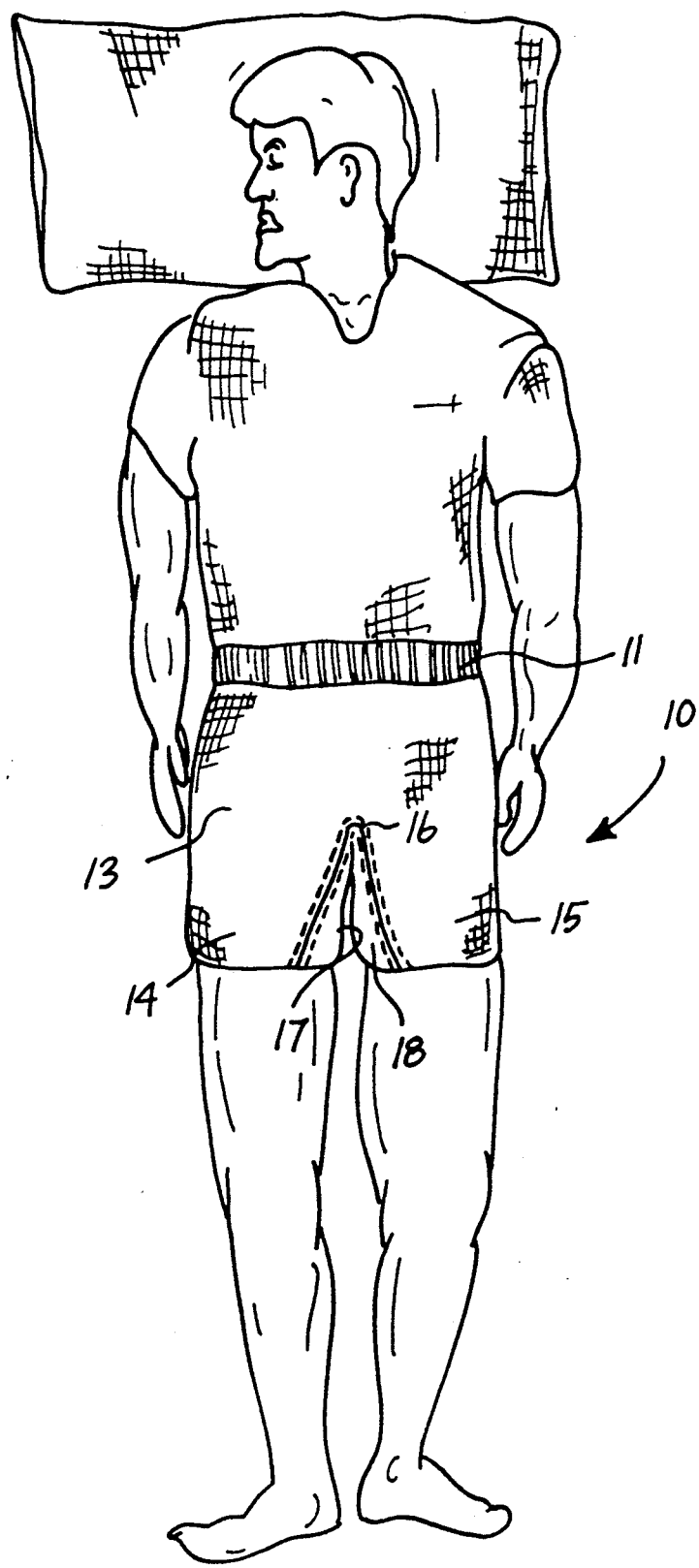
FIG. 1 is an orthographic frontal view of the instant invention worn by an individual during slumber.
Figure 2:
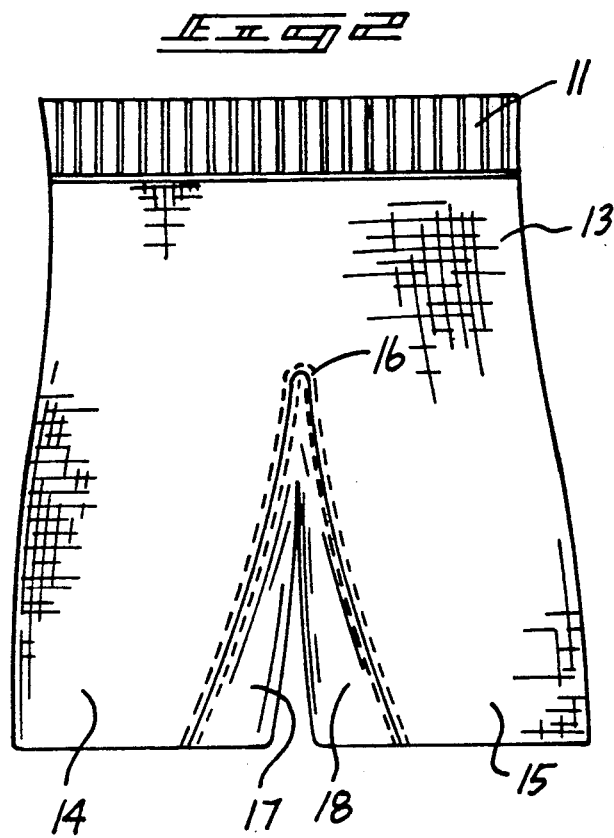
FIG. 2 is an orthographic frontal view of the invention, taken in elevation.

With reference now to the drawings, and in particular to FIGS. 1 to 8 thereof, a new and improved hip alignment garment embodying the principles and concepts of the present invention and generally designated by the reference numerals 10 and 10a will be described.

Figure 3:
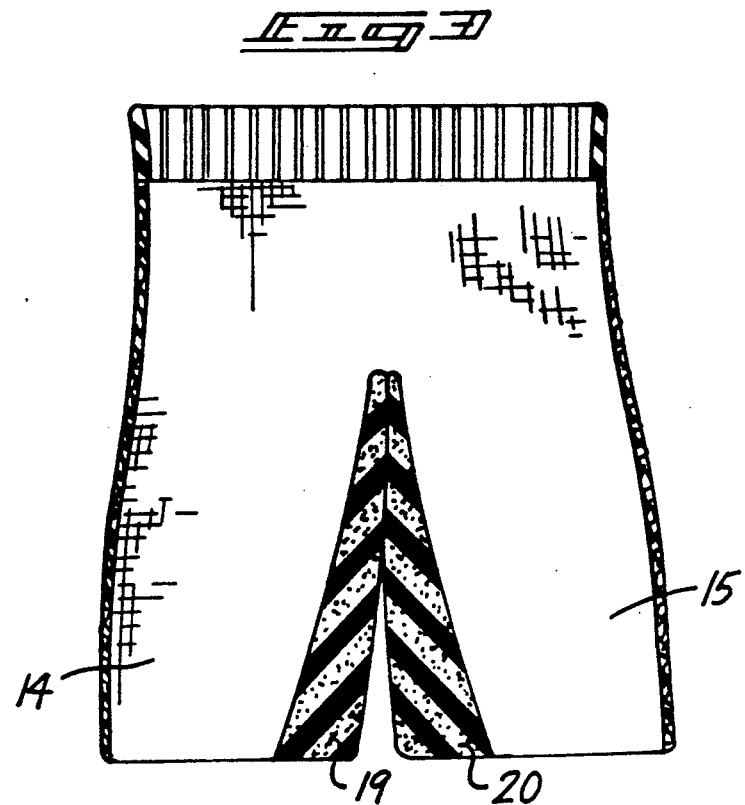
FIG. 3 is an orthographic cross-sectional illustration of the instant invention.

More specifically, the hip alignment garment 10 of the instant invention essentially comprises a pants-like garment member defined by a torso encompassing portion 13 formed with a continuous elastometric hip band 11 at its upper terminal end defining a cylindrical torso receiving entrance. A right and left leg member 14 and 15 respectively extend downwardly from the torso portion 13 joined at a joinder intersection 16 or a crotch portion medially of the torso portion 13. The right and left leg members 14 and 15 each respective right and left interior arcuate surfaces 17 and 18 that are positioned in confronting relationship relative to one another, as illustrated in FIG. 1 for example. Reference to FIG. 3 notes the use of a right and left wedge-shaped pads 19 and 20 mounted within the respective right and left interior arcuate surfaces 17 and 18 to effect spreading of the leg portions of an individual during slumber for proper spacing on the legs in lieu of a pillow or the like typically utilized for such purposes. The right and left wedge-shaped pads 19 and 20 are typically formed of an elastomeric type construction.

Figure 4:
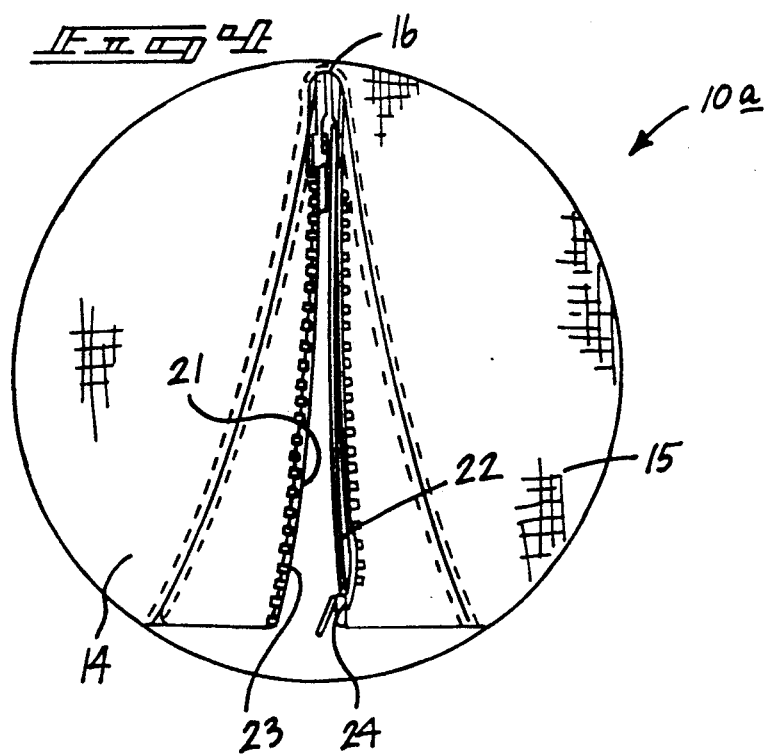
FIG. 4 is an orthographic enlarged partial view of the confronting interior leg surface of a modification of the instant invention.
Figure 5:
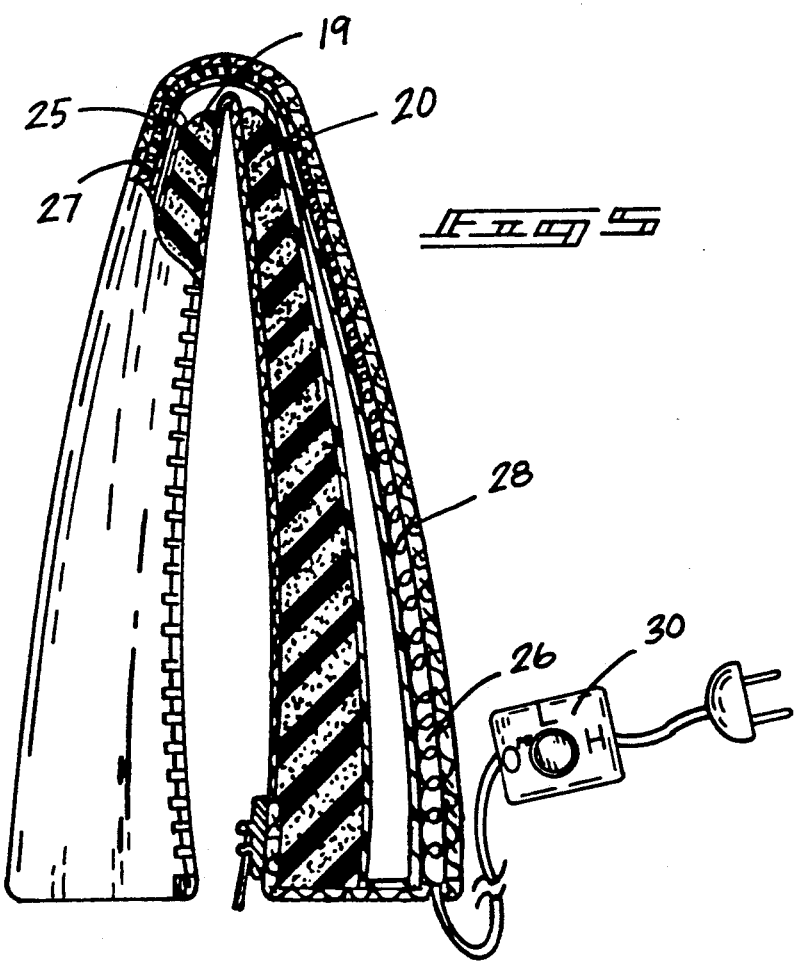
FIG. 5 is an enlarged orthographic view, partially in section, of the confronting leg portions of the modified aspect of the instant invention.

FIGS. 4 and 5 illustrate the use of a right and left pocket 21 and 22 formed at the right and left interior arcuate surfaces 17 and 18, wherein the right and left pockets 21 and 22 are in confronting relationship with confronting and respective right and left zippers 23 and 24 providing access interiorly of the pockets to effect removal of the wedge-shaped pads 19 and 20. Optionally, a respective right and left inflation or pneumatic wedge-shaped chamber 19a and 20a may be provided (see FIGS. 7 and 8), wherein each pneumatic chamber 19a and 20a respectively includes a respective right and left inflation valve 31 and 32 to permit respective and selective inflation of each of the pneumatic chambers that may subsequently be inserted into the respective right and left pocket 21 and 22. Further, a "U" shaped continuous chamber is defined rearwardly of the right and left pockets 21 and 22 of a continuous construction and defining a respective right and left pad receiving chamber 25 and 26 respectively. The right and left pad receiving chambers 25 and 26 are directed in contiguous relationship relative to the joinder intersection or crotch portion 16. Within the right and left pad receiving chambers 25 and 26 are mounted a respective right and left heating pad 27 and 28 joined together by electrical connector 29 that is positioned adjacent the joinder intersection 16, with the right and left heating pads 27 and 28 controlled by a control rheostat 30. In this manner, selective heating of the thigh portions of an individual may be utilized in assisting blood circulation in that portion of the body.

As to the manner of usage and operation of the instant invention, the same should be apparent from the above disclosure, and accordingly no further discussion relative to the manner of uasage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and directed to be protected by Letters Patent of the United States is as follows:

1. A hip alignment garment comprising,
    a pants garment member, including a torso encompassing portion, the torso encompassing portion includes a continuous elastomeric hip band formed at an upper terminal end of the torso encompassing portion, and
    the torso encompassing portion further including a respective right and left leg member, the right and left leg members each include a respective right and left interior arcuate surface that are positioned in confronting relationship relative to one another between the right and left leg members, and the right and left leg members joined to the torso encompassing portion at a crotch portion, and
    a right wedge-shaped pad mounted within the right leg member within the right arcuate surface, and
    a left wedge-shaped pad mounted within the left leg member within the left arcuate surface, and
    the right arcuate surface includes a right pocket and the left arcuate surface includes a left pocket, wherein the right pocket includes a left zipper, wherein the right and left zippers are arranged in confronting relationship relative to one another to define access to the respective right and left pockets, and the right wedge-shaped pad removably mounted within the right pocket and the left wedge-shaped pad removably mounted within the left pocket.

2. An apparatus as set forth in claim 1 wherein the right wedge-shaped pad defines a right wedge-shaped pneumatic chamber and the left wedge-shaped pad defines a left wedge-shaped pneumatic chamber, wherein the right wedge-shaped pneumatic chamber includes a right inflation valve, and the left wedge-shaped pneumatic chamber includes a left inflation valve, wherein the right and left inflation valves are adapted to permit selective inflation of the right and left wedge shaped pneumatic chambers.

3. An apparatus as set forth in claim 2 wherein the right pocket includes a right pad receiving chamber positioned adjacent the pocket coextensive therewith, and the left pocket includes a left pad receiving chamber adjacent to and coextensive with the left pocket, wherein the right and left pad receiving chambers are intercommunicated by a conduit defining a "U" shaped continuous chamber, and the right pad receiving chamber includes a right heating pad, and the left pad receiving chamber includes a left heating pad and an electrical connector directed through the conduit, and a control rheostat in operative association with the right and left heating pads to effect selective heating of the right and left heating pads to enhance blood circulation when the garment is worn by an individual.

* * * * *